United States Patent [19]

Yoshimura et al.

[11] Patent Number: 4,510,331

[45] Date of Patent: Apr. 9, 1985

[54] PROCESSES FOR PRODUCING 7-OCTEN-1-AL AND DERIVATIVES THEREOF

[75] Inventors: Noriaki Yoshimura; Masuhiko Tamura, both of Kurashiki, Japan

[73] Assignee: Kuraray Company, Ltd., Kurashiki, Japan

[21] Appl. No.: 390,984

[22] Filed: Jun. 22, 1982

[51] Int. Cl.³ .............................................. C07C 45/67
[52] U.S. Cl. ...................................... 568/450; 568/906; 568/485; 564/463; 564/469; 260/404; 260/406
[58] Field of Search ............... 568/450, 481, 448, 485, 568/906

[56] References Cited

U.S. PATENT DOCUMENTS

| | | | |
|---|---|---|---|
| 2,046,556 | 7/1936 | Groll et al. | 568/450 |
| 2,683,175 | 7/1954 | Himel et al. | 568/450 |
| 2,815,379 | 12/1957 | Surmatis | 568/448 |
| 2,997,154 | 10/1937 | Groll et al. | 568/450 |
| 4,132,675 | 1/1979 | Näf | 568/448 |

*Primary Examiner*—Werren B. Lone
*Attorney, Agent, or Firm*—Oblon, Fisher, Spivak, McClelland & Maier

[57] ABSTRACT

There are disclosed a process for producing 7-octen-1-al which comprises isomerizing 2,7-octadien-1-ol in the presence of a catalyst comprising oxides of at least two metals selected from the group consisting of copper, chromium and zinc and processes for producing derivatives of 7-octen-1-al.

4 Claims, No Drawings

PROCESSES FOR PRODUCING 7-OCTEN-1-AL AND DERIVATIVES THEREOF

BACKGROUND OF THE INVENTION

1. Field of the Invention

This invention relates to processes for producing 7-octen-1-al and derivatives thereof starting from 2,7-octadien-1-ol.

2. Description of the Prior Art

7-Octen-1-al has two very reactive functional groups, namely the terminal vinyl group and the formyl group, and accordingly is very useful as the starting material for synthesizing a variety of industrially useful compounds. However, lack of an established, advantageous production process has prevented said compound from being produced on a commercial scale. A known process for synthesizing 7-octen-1-al comprises hydroboration of 1,7-octadiene followed by oxidation of the resulting 7-octen-1-ol [Tetrahedron Letters, No. 36, pp. 3329–3332 (1978)]. However, this process is disadvantageous in that such very expensive reagents as 9-borabicyclononane and pyridium chlorochromate are required for the hydroboration and oxidation and that the yield of 7-octen-1-al is as low as about 60% based on the reacted 1,7-octadiene.

SUMMARY OF THE INVENTION

Accordingly, an object of the present invention is to provide a process for producing 7-octen-1-al in an industrially advantageous manner.

Another object of the present invention is to provide a method of synthesizing 7-octen-1-al in high yield starting from a readily available material.

Still another object of the present invention is to provide processes for producing a variety of industrially useful compounds starting from 7-octen-1-al.

It has now been found that treatment of 2,7-octadien-1-ol in the presence of a catalyst comprising oxides of at least two metals selected from the group consisting of copper, chromium and zinc gives 7-octen-1-al in high yield as a result of selective isomerization involving the allylic double bond alone. It has also been found that 7-octen-1-al can easily be converted to the compounds shown below via the synthetic routes shown below.

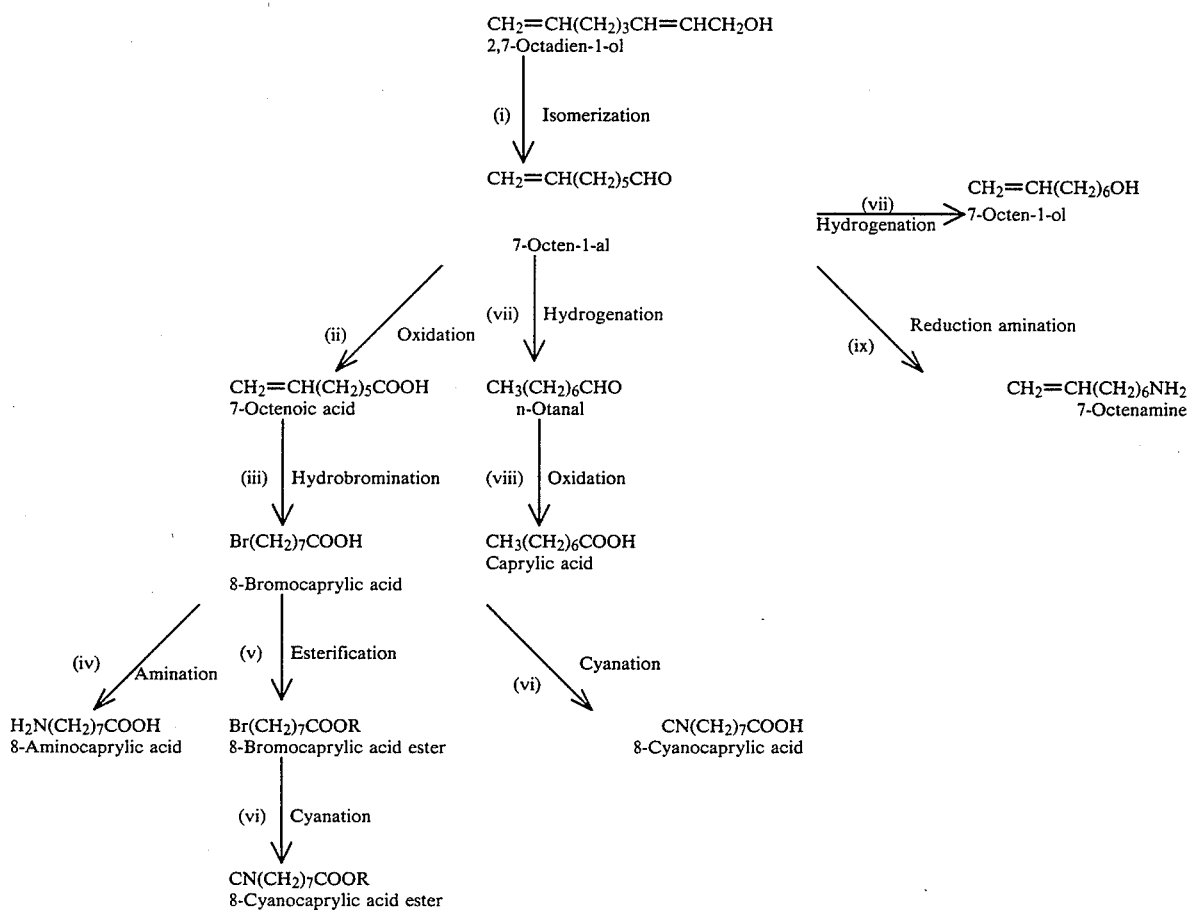

The invention will be understood more clearly by referring to the description which follows.

DETAILED DESCRIPTION OF THE INVENTION

The starting material, in the processes in accordance with the invention, namely 2,7-octadien-1-ol, can be produced in an industrially easy manner by reacting butadiene with water in the presence of a palladium catalyst according to the present inventors' previous proposal [GB No. 2074156A and DE No. 3112213].

Isomerization of 2,7-octadien-1-ol (step i)

The catalyst comprising oxides of at least two metals selected from the group consisting of copper, chromium and zinc to be used for this isomerization reaction includes those capable of acting as dehydrogenation catalysts, such as copper- and chromium-containing oxides (e.g. copper chromite, or copper-chromium oxide), copper- and zinc-containing oxides (e.g. copper-zinc oxide), zinc- and chromium-containing oxides (e.g. zinc chromite, or zinc-chromium oxide) and copper-, chromium and zinc-containing oxides (e.g. copperchromium-zinc oxide). The metal oxide catalysts mentioned above are generally used in the (petro) chemical industry as dehydrogenation catalysts and are easily available as commercial products. They may also be prepared by the methods described, for example, in Organic Synthesis Collective Volume II, 142 (1943), J. Am. Chem. Soc., 54, 1138 (1932), ibid., 58, 1053 (1963), Ind. Eng. Chem. 27, 134 (1935), and ibid., 21, 1052 (1929). These catalysts may be modified in part with one or more other metal components such as tungsten, molybdenum, rhenium, zirconium, manganese, titanium, iron, barium, magnesium and calcium. The catalysts may be supported on a carrier such as alumina, silica and diatomaceous earth. These catalysts may be used either each alone or in combination of two or more. For increasing the catalytic activity, the catalysts may be pretreated with hydrogen. In some cases, coexistence of an adequate amount of one or more of sulfur compounds, antimony compounds, bismuth compounds, phosphorus compounds, nitrogen compounds and so on for partial poisoning of the catalyst may result in an increase in selectivity for the isomerization of 2,7-octadien-1-ol to 7-octen-1-al. The above-mentioned sulfur compounds include sulfur, sodium sulfate, etc., the antimony compounds include antimonous oxide, etc., the bismuth compounds include bismuth oxide, etc., the phosphorus compounds include phosphoric acid, triphenylphosphine, etc., and the nitrogen compounds include pyridine, aniline, etc. If, for example, palladium catalysts, nickel catalysts, cobalt catalysts, rhodium catalysts and platinum catalysts, which are generally used in common double bond isomerization and hydrogenation reactions, are used in the isomerization of 2,7-octadien-1-ol, not only the yield of 7-octen-1-al is low but the yield of various byproducts substantially incapable of being separated from 7-octen-1-al is high. Accordingly, such catalysts cannot be used in the production of 7-octen-1-al by isomerization of 2,7-octadien-1-ol.

The isomerization reaction is preferably carried out in an atmosphere of a gas which is inert under the reaction conditions, such as nitrogen, carbon dioxide, helium or argon. The whole or part of the inert gas may be replaced with hydrogen gas. When the reaction is carried out in the copresence of hydrogen, the hydrogen partial pressure is preferably kept below 10 atmospheres. At a hydrogen partial pressure exceeding 10 atmospheres, the hydrogenation reaction prevails, unfavorably causing decrease in the selectivity toward 7-octen-1-al. The reaction temperature is selected within the range of 100°–250° C., preferably 130°–220° C. The reaction may be carried out in the liquid or gaseous phase either continuously or batchwise in a stirred tank reactor, bubble tower reactor or packed tower reactor. In the case of liquid phase reaction, the starting material 2,7-octadien-1-ol or the product 7-octen-1-al may function as the solvent. The reaction may also be conducted using an organic solvent which is inert under the reaction conditions. Usable organic solvents are saturated aliphatic hydrocarbons (e.g. hexane, octane, decane, liquid paraffin), saturated alicyclic hydrocarbons (e.g. cyclohexane, methylcyclohexane), aromatic hydrocarbons (e.g. benzene, toluene, xylene, biphenyl), ethers (e.g. diisopropyl ether, dibutyl ether, dioctyl ether, diphenyl ether, tetrahydrofuran, diethylene glycol diethyl ether, polyethylene glycol dimethyl ether), alcohols (e.g. ethanol, butanol, octanol, ethylene glycol, glycerol, polyethylene glycol), and so on.

7-Octen-1-al produced by the present process has a lower boiling point than the starting material 2,7-octadien-1-ol. Therefore, in an especially preferred mode of practice, the reaction is carried out while removing 7-octen-1-al from the reaction system at an atmospheric pressure or under reduced pressure (reaction with simultaneous distillation), whereby the formation of byproducts is greatly suppressed. For attaining an increased 7-octen-1-al selectively, it is also effective to carry out the reaction in the gaseous or liquid phase while continuously passing 2,7-octadien-1-ol through a reactor packed with a isomerization catalyst in a manner such that the contact time is short. 7-Octen-1-al can be recovered from the liquid reaction mixture (in the case of gaseous phase reaction, the condensate) or the distillate by a conventional distillation procedure. Not only isolated 7-octen-1-al but also the liquid reaction mixture or distillate as it is can be used in the subsequent reaction steps.

Oxidation of 7-octen-1-al (step ii)

7-Octen-1-al is contacted with an oxygen-containing gas in the presence of an oxidation catalyst and an organic solvent so that it is converted to 7-octenoic acid. The oxygen-containing gas is, for example, oxygen gas, air, a mixture of nitrogen and oxygen in an arbitrary ratio, or a mixed gas composed of any of these and carbon dioxide. The reaction pressure varies depending on the oxygen content in the oxygen-containing gas and accordingly cannot be specified in a definite manner. Generally, however, the pressure is selected within the range of 1–15 atmospheres (absolute). The oxidation catalyst may be any of those metal salts that are per se known as catalysts for aldehyde oxidation, such as cobalt salts, manganese salts, nickel salts, copper salts and iron salts. In consideration of solubility in the the liquid reaction mixture, corrosiveness to reaction apparatus and availability, aliphatic monocarboxylic acid metal salts are preferred. Among them, aliphatic monocarboxylic acid salts of copper or iron are especially preferred as the oxidation catalysts from the viewpoints of rate of reaction, selectivity of reaction, availability, solubility in the liquid reaction mixture and so on. These oxidation catalysts may be used alone or in combination of two or more. The oxidation catalysts are generally used in an amount of 0.01–50 millimoles per liter of the liquid reaction mixture. Organic solvents usable in the oxidation reaction include aliphatic hydrocarbons (e.g. pentane, hexane, heptane, octane), aromatic hydrocarbons (e.g. benzene, toluene, xylene), ketones (e.g. acetone, methyl ethyl ketone), aliphatic monocarboxylic acids (e.g. acetic acid, propionic acid, butyric acid, valeric acid, hexanoic acid, heptanoic acid) and aliphatic monocarboxylic acid esters (e.g. methyl, ethyl, n-propyl, isopropyl and n-butyl esters of the aliphatic monocarboxylic acids mentioned above by way of example). The reaction temperature is selected generally within the range of about 10°–120° C., preferably 30°–80° C. This oxidation reaction is carried out by bringing a solution of 7-octen-1-al in a reaction solvent into contact with an oxygen-containing gas either continuously or intermittently. No particular limitations are placed on the 7-octen-1-al concentration in the liquid reaction mixture. However, when the reaction is carried out while maintaining the concentration at 1 mole per liter or below, accumulation of heat of reaction can be avoided, side reactions such as polymerization of 7-octen-1-al can be suppressed and the selectivity of reaction can be increased. For increasing the selectivity of reaction, it ia also preferable to carry out the reaction so that the conversion of 7-octen-1-al to 7-octenoic acid does not exceed about 80%. As the reactor, there may generally be used a stirred tank reactor or a bubble tower reactor. After the reaction, following removal of the oxidation catalyst by a conventional method as necessary, highly pure 7-octenoic acid can be isolated from the liquid reaction mixture by distillation or recrystallization.

7-Octenoic acid is a compound useful as the starting material in the production of 8-aminocaprylic acid and cation exchange membranes or films and also as the starting material in various organic syntheses, for example, of vinyl polymer modifiers and exaltone.

Hydrobromination of 7-octenoic acid (step iii)

Anti-Markovnikov addition of hydrogen bromide converts 7-octenoic acid to 8-bromocaprylic acid. The anti-Markovnikov radical addition of hydrogen bromide to the terminal C=C double bond is a well-known old reaction and the so-far known procedures and reaction conditions can be used also in the practice of the present invention. Thus, the addition of hydrogen bromide to 7-octenoic acid is effected at a temperature of $-10°$ C. to $+70°$ C., preferably $0°-50°$ C., in a nonpolar solvent in the presence of molecular oxygen and/or a free radical catalyst. Though possible, the method comprising carrying out the reaction at low temperatures using ultraviolet light as the free radical generator is expensive, hence undesirable from the industrial standpoint. A very large number of free radical catalysts may be used in carrying out this reaction. Most representative examples are ozone, lauroyl peroxide, benzoyl peroxide and tert-butyl peroxide. These free radical catalysts are used in an amount of about 0.01-10 mole percent based on 7-octenoic acid. When molecular oxygen is used, it may be diluted with an inert gas such as nitrogen, helium or argon, and air itself may also be used. Molecular oxygen is used in an amount of not less than 0.001 mole per mole of 7-octenoic acid. Though there is no critical upper limit to the amount of oxygen, it is generally desirable to feed 0.01-1 mole of oxygen per mole of 7-octenoic acid to the reaction system. The addition of hydrogen bromide to 7-octenoic acid may also be effected in the copresence of the above-mentioned free radical catalyst and oxygen. Since this reaction proceeds via the bromine radical, it is naturally recommendable to avoid coexistence of a substance capable of catching bromine radicals in the reaction system. For increasing the selectivity of reaction and allowing the reaction to proceed smoothly, the reaction is generally carried out in a nonpolar solvent while keeping the concentration of 7-octenoic acid at a relatively low level. Usable nonpolar solvents are, for example, saturated aliphatic hydrocarbons (e.g. pentane, hexane, heptane, octane, ligroin), substituted or unsubstituted aromatic hydrocarbons (e.g. benzene, toluene, xylene, chlorobenzene) and halogenated hydrocarbons (e.g. dichloromethane, carbon tetrachloride, dichloroethane). Hydrogen bromide is fed to the reactor either in the gaseous form or in the form of a solution in the same nonpolar solvent as is used as the reaction solvent.

For increasing the selectivity toward 8-bromocaprylic acid, it is desirable to maintain the hydrogen bromide concentration in the reaction system within the range of 1-10 moles per mole of 7-octenoic acid. Since the reaction is exothermic, the reaction is preferably carried out while feeding 7-octenoic acid and, as necessary, hydrogen bromide continuously or intermittently in a manner such that the 7-octenoic acid concentration in the reaction system remains not more than 2 moles per liter, preferably not more than 1 mole per liter. After the reaction, 8-bromocaprylic acid is recovered from the liquid reaction mixture by a usual distillation procedure. Recrystallization especially from a saturated aliphatic hydrocarbon gives highly pure 8-bromocaprylic acid. When a saturated aliphatic hydrocarbon is used as the reaction solvent, 8-bromocaprylic acid crystallizes out as the reaction proceeds, and the crystals may be collected by such a procedure as filtration, sedimentation or centrifugation and fed to the next reaction step without any further purification.

Amination of 8-bromocaprylic acid (step iv)

8-Bromocaprylic acid is converted to 8-aminocaprylic acid by reaction with ammonia. Liquid ammonia or an aqueous solution of ammonium hydroxide is used as the ammonia source. Use of a large excess of ammonia or ammonium hydroxide as compared with 8-bromocaprylic acid is effective in increasing the selectivity of reaction, and in this case ammonia or ammonium hydroxide simultaneously functions as the reaction solvent. Like usual amination reactions, this reaction is preferably conducted in the liquid phase at a temperature of $0°-150°$ C., preferably $20°-100°$ C. In a desirable mode of practice, an ammonium salt, typically ammonium carbonate, ammonium chloride or ammonium bromide, is allowed to coexist in the reaction system in an amount of about 2-10 moles per mole of 8-bromocaprylic acid so that the possible secondary reaction between the 8-aminocaprylic acid resulting from the reaction and the starting material 8-bromocaprylic acid can be minimized. The reaction may also be carried out in the presence of an organic solvent inert under the reaction conditions. Among usable organic solvents, there are methanol, ethanol, propanol, butanol, ethylene glycol, propylene glycol, diethylene glycol, polyethylene glycol, diglyme and triglyme. These solvents are used in a volume ratio to liquid ammonia or aqueous ammonium hydroxide of 0.1-10. After the reaction, the reaction mixture is neutralized with a basic substance, typically an alkali metal hydroxide or an alkali metal alcoholate, as necessary, and then 8-aminocaprylic acid is recovered by a conventional separation procedure. When 8-aminocaprylic acid is to be recovered from an aqueous solution, 8-aminocaprylic acid can be separated as a precipitate by adjusting the pH of the aqueous solution to 5.5 to 6.5. Highly pure 8-aminocaprylic acid which can be used as the starting material for the manufacture of 8-nylon without any further purification can be obtained by recrystallization from water.

It is known for long that 8-nylon possesses interesting fundamental performance characteristics as compared with other nylons and can be produced by polymerizing caprylolactam. However, caprylolactam, the monomer for the manufacture of 8-nylon, which, in the prior art process, is produced in a very complicated manner via steps of synthesis of cyclooctadiene by dimerization of butadiene, hydrogenation, oxygen oxidation, dehydrogenation, oximation and Beckmann rearrangement, is very expensive and accordingly has not been produced on a commercial scale. In addition, it is generally considered that polymerization of lactams is difficult as compared with polymerization of the corresponding amino acids. In accordance with the process of present invention, 8-aminocaprylic acid can be produced in an industrially advantageous manner starting from 2,7-octadien-1-ol and via the steps of isomerization, oxygen oxidation, bromination and amination.

Esterification of 8-bromocaprylic acid (step v)

The esterification of 8-bromocaprylic acid is conducted by a known method by contacting 8-bromocaprylic acid with an alcohol in the presence of an acid catalyst. Examples of the alcohol usable for the esterification are methanol, ethanol, n-propanol, n-butanol, 2-ethylhexanol, n-octanol and other aliphatic alcohols. As the acid catalyst, there may be used such a mineral acid as sulfuric acid, phosphoric acid or hydrochloric acid or an ion exchange resin in an amount of 1–20 percent based on 8-bromocaprylic acid. The reaction temperature is selected within the range of 20°–150° C. After the reaction, the 8-bromocaprylic acid ester is recovered from the liquid reaction mixture by a usual distillation procedure.

Cyanation of 8-bromocaprylic acid or an ester thereof (step vi)

8-Bromocaprylic acid is converted to 8-cyanocaprylic acid by reaction with an alkali metal cyanide and an ester of 8-bromocaprylic acid to the corresponding ester of 8-cyanocaprylic acid by reaction with an alkali metal cyanide. The reaction between 8-bromocaprylic acid and an alkali metal cyanide is carried out in water and/or a polar organic solvent in the presence or absence of a catalyst. 8-Bromocaprylic acid may also be used in the form of an alkali salt which results from treatment of 8-bromocaprylic acid with sodium or potassium hydroxide, carbonate or bicarbonate. The alkali metal cyanide includes lithium cyanide, sodium cyanide and potassium cyanide. The alkali metal cyanide is used in an amount of 1–5 moles, preferably 1.2–3 moles, per mole of the 8-bromocaprylic acid alkali metal salt. Polar solvents usable in the reaction include acetonitrile, dimethyl sulfoxide, dimethylformaide, hexamethylphosphoramide, sulfolane, methanol, ethanol, ethylene glycol, polyethylene glycol, diethylene glycol dimethyl ether and polyethylene glycol dimethyl ether. These solvents may be used alone or in admixture with water in an arbitrary ratio. The reaction is carried out at a temperature of from room temperature to about 150° C., preferably within the range of 40°–100° C. Although the reaction can be carried out in the absence of a catalyst, the use of a catalyst can advantageously promote the reaction. Usable catalysts include quaternary ammonium salts (e.g. tetrabutylammonium bromide, tetrabutylammonium iodide, benzyltriethylammonium chloride), quaternary phosphonium salts (e.g. tetrabutylphosphonium chloride, ethyltrioctylphosphonium bromide, hexadecyltributylphosphonium bromide), crown ethers and cryptates (e.g. 18-crown, dibenzo-18-crown, dicyclohexyl-18-crown, diaza-18-crown) and polyetylene glycol derivatives (e.g. polyethylene glycol with average molecular weight of 200–2,000, polyethylene glycol monoalkyl ether, polyethylene glycol dialkyl ether). These catalysts are used generally in a concentration of 0.1–100 millimoles per liter of the liquid reaction mixture. After the reaction, 8-cyanocaprylic acid is isolated from the liquid reaction mixture by a conventional procedure.

The above description for the reaction of an alkali metal salt of 8-bromocaprylic acid with an alkali metal cyanide also applies to the reaction of an ester of 8-bromocaprylic acid with an alkali metal cyanide. From the viewpoint of product separability, it is especially preferable to carry out the reaction of an ester of 8-bromocaprylic acid with an alkali metal cyanide in the presence of a catalyst such as mentioned above in a manner such that the aqueous alkali metal cyanide solution and the 8-bromocaprylic acid ester form a heterogeneous system. For the purpose of increasing the product separability, the reaction can also be conducted in the copresence of a hydrophobic organic solvent inert to the reaction. Examples of the solvent usable for such purpose are hydrocarbons (e.g. hexane, heptane, octane, benzene, toluene, xylene) and halobenzenes (e.g. chlorobenzene, dichlorobenzene). After the reaction, the 8-cyanocaprylic ester is recovered from the liquid reaction mixture by a conventional procedure.

8-Cyanocaprylic acid and esters thereof are useful as intermediates for the synthesis of useful substances including 9-nylon and azelaic acid.

Hydrogenation of 7-octen-1-al (step vii)

When subjected to hydrogenation treatment in the presence of a hydrogenation catalyst and hydrogen, 7-octen-1-al is converted to n-octanal (n-octylaldehyde) as a result of hydrogenation of the C=C double bond. The catalyst to be used in this reaction is a per se known catalyst. Specific examples of the catalyst are palladium black, palladium catalysts supported on charcoal, silica, alumina, etc., Raney nickel, modified Raney nickel, nickel-on-diatomaceous earth, platinum black, platinum-on-carrier and rhodium-on-carrier. Especially preferred among them is palladium-on-carbon, having regard to such factors as selectivity of reaction and mildness of reaction conditions. The hydrogenation of 7-octen-1-al is generally carried out in the liquid phase. It is advantageous from the industrial viewpoint to make the starting material, byproduct or product (n-octanal) or a mixture of these in an arbitrary ratio simultaneously serve as the solvent. As necessary, however, such solvents as hydrocarbons, alcohols, esters and ethers may be used. The optimal range each of the hydrogen pressure and reaction temperature depends on the kind of catalyst and accordingly cannot be specified in a definite manner. Generally, however, the known conditions commonly employed in hydrogenating C=C double bond-containing compounds can be used also in the hydrogenation of 7-octen-1-al. Thus, the hydrogen pressure is generally selected within the range of 1–15 atmospheres, and the reaction temperature within the range of from room temperature to 250° C., preferably within the range of 30°–200° C. A usual fractional distillation procedure following removal of the catalyst from the hydrogenation reaction mixture gives highly pure n-octanal in high yield. The byproduct formed in the hydrogenation of 7-octen-1-al is mainly composed of n-octanol. However, the formation of n-octanol as a byproduct causes no difficulty because n-octanol and n-octanal can very easily be separated from each other. From this viewpoint as well, establishment of optimal reaction conditions for 7-octen-1-al hydrogenation is relatively easy.

Although n-octanal is useful as a perfumery chemical and as the starting material for the manufacture of caprylic acid, n-octylamine, n-octanol, 2-hexyldecanol, 2-hexyldecanoic acid, etc., any industrially advantageous processes for its production have not been established. At present, n-octanal is commercially produced in small quantities through a very complicated process comprising hydrogenation of caprylic acid derivatives contained in natural glycerides and dehydrogenation of the thus-obtained n-octanol. On the contrary, the process of the present invention can produce n-octanal in a simple and industrially advantageous manner by isomerizing 2,7-octadien-1-ol and hydrogenating the resulting 7-octen-1-al under those conditions under which the carbon-to-carbon double bond can be hydrogenated.

When the hydrogenation of 7-octen-1-al is carried out at 70° C.–150° C. in the presence of a chromium oxide catalyst and hydrogen, 7-octen-1-ol is preferentially produced. The chromium oxide catalyst to be used in this reaction includes among others the same copper chromite and zinc chromite catalysts as mentioned above for the catalysts for isomerization of 2,7-octadien-1-ol to 7-octen-1-al, and may partly be modified with one or more metal components selected from among tungsten, molybdenum, rhenium, zirconium, nickel, manganese, titanium, iron, barium, magnesium, calcium, etc. and furthermore may be supported on such a carrier as alumina, silica or diatomaceous earth. Commercially available catalysts may be used as they are. In addition, the catalyst may be prepared, for example, by the methods described in Organic Syntheses Coll. Vol. II, 142 (1943) and Ind. Eng. Chem., 27, 134 (1935). Pretreatment of the catalyst with hydrogen increases the catalytic activity. When the reaction is carried out in the liquid phase, the catalyst is used in an amount of 0.1–25 percent by weight, preferably 0.5–10 percent by weight, as metal, based on 7-octen-1-al. If such general-purpose hydrogenation catalysts as palladium, nickel, cobalt, rhodium and platinum catalysts are used in hydrogenating 7-octen-1-al, there are obtained n-octanol and n-octanal as a result of C=C double bond hydrogenation whereas no substantial quantity of 7-octen-1-ol is obtained.

In carrying out the reaction, the hydrogen pressure is selected within the range of 1–200 atmospheres, preferably 10–100 atmospheres. In this step according to the invention, the reaction temperature is a very important factor and strongly governs the selectivity toward 7-octen-1-ol. Only when the reaction is performed at a temperature within the range of 70°–150° C., practicable selectivity toward 7-octen-1-ol can be obtained. A preferable reaction temperature range is 100°–130° C. At temperatures below 70° C., the rate of reaction is extremely slow; at temperatures above 150° C., the yield of n-octanol, which can be separated from 7-octen-1-ol with difficulty, unfavorably increases. The present inventors' investigation has revealed that, under the reaction conditions, the C=C double bond hydrogenation tends to occur following the formyl group hydrogenation. Therefore, the selectivity toward 7-octen-1-ol can further be increased by stopping the reaction when the hydrogen absorption has reached the quantity required for the formyl group hydrogenation only (for batchwise reaction). Another method to increase the selectivity toward 7-octen-1-ol is to suppress the conversion of 7-octen-1-al to a certain extent. The hydrogenation reaction in accordance with the present invention may be carried out either in the absence of a solvent, that is by making the starting material and reaction product serve as the solvents, or in the presence of a solvent inert to the reaction. Usable solvents include alcohols (e.g. methanol, ethanol, propanol, butanol, octanol), hydrocarbons (e.g. hexane, heptane, octane, benzene, toluene, xylene) and ethers (e.g. diethyl ether, dibutyl ether, diethyleneglycol dimethyl ether, tetrahydrofuran). The hydrogenation reaction may be carried out either batchwise or continuously. The reactor may be an industrially common stirred tank, bubble tower or packed tower reactor. After the reaction, highly pure 7-octen-1-ol can be recovered from the liquid reaction mixture of fractional distillation following removal of the catalyst.

7-Octen-1-ol not only can easily be converted to 8-chloro-1-octene, 9-hydroxynonanal, 1,8-dihalooctane and so on but also itself is useful as a polymer modifier. Furthermore, it is useful as an intermediate for the manufacture of agricultural chemicals, medicines, perfumery chemicals, etc. In the so far proposed method of synthesizing 7-octen-1-ol which comprises hydroborating 1,7-octadiene (Tetrahedron Letters, 1978, 3329), a very expensive reagent, namely 7-borabicyclononane, is required, and therefore the method cannot be accepted as an industrial method of producing 7-octen-1-ol. On the other hand, in accordance with the present invention, 7-octen-1-ol can be produced in an industrially advantageous manner through a process comprising isomerizing 2,7-octadien-1-ol and hydrogenating the resulting 7-octen-1-al.

Oxidation of n-octanal (step viii)

n-Octanal is converted to caprylic acid by oxidation effected by bringing n-octanal into contact with oxygen gas or an oxygen-containing gas in the presence of an oxidation catalyst and preferably in the presence of an organic solvent. As the oxygen-containing gas, there may be used air, a mixed gas composed of nitrogen and oxygen in an arbitrary ratio, or a mixture thereof with helium gas, argon gas, carbon dioxide or the like. The reaction temperature is selected within the range of from room temperature to 120° C., especially preferably within the range of 30°–90° C. The oxidation catalyst may be any of those metal salts that are known to be suited as aldehyde oxidation catalysts, such as cobalt salts, manganese salts, nickel salts, copper salts and iron salts. Preferable metal salts are aliphatic monocarboxylic acid metal salts in view of their solubility in the liquid reaction mixture, corrosiveness to reaction apparatus and easy availability. Among them, aliphatic monocarboxylic acid salts of copper or iron are especially preferred as the oxidation catalysts from the viewpoints of rate of reaction, selectivity of reaction, availability and solubility in the liquid reaction mixture, among others. These oxidation catalysts may be used either alone or in combination of two or more. The oxidation catalysts are generally used in an amount of 0.01–10 milligram atoms as metal per liter of the liquid reaction mixture. The use of the product, namely caprylic acid, as the organic solvent is most desirable from the industrial standpoint. Other carboxylic acids such as acetic, propionic and butyric acid may also be used as the organic solvents either alone in place of caprylic acid or together with caprylic acid.

The oxygen oxidation of n-octanal is generally carried out by feeding oxygen gas or an oxygen-containing gas and n-octanal either continuously or intermittently into a reaction solvent containing an oxidation catalyst dissolved therein. The reactor may be any of those commonly used in gas-liquid contact reactions, such as a stirred tank reactor, a bubble tower reactor and a perforated plate tower reactor. The reaction pressure varies depending on the oxygen content in the oxygen-containing gas and the reaction temperature and accordingly cannot be specified in a definite manner. Generally, however, the pressure is selected within the range of 1–20 atmospheres (absolute). After the reaction, highly pure caprylic acid can be isolated from the liquid reaction mixture by a conventional distillation procedure. It is desirable to decompose peroxides contained in trace amounts in the liquid reaction mixture by heat treatment and/or treatment with a catalyst of said mixture prior to the distillation procedure.

Caprylic acid is useful as a starting material for the manufacture of metal soaps, driers, lubricants, etc. Although caprylic acid is present in small amounts in natural glycerides, a very complicated process is required for isolation thereof and at present the acid is not yet produced on a large commercial scale. With such background, 2-ethylhexanoic acid, which is poor in biodegradability and stability against oxidation, is now used as a $C_8$-monocarboxylic acid and as a caprylic acid substitute. In accordance with the invention, caprylic acid can be obtained in high yield in a simple manner by isomerizing 2,7-octadien-1-ol, hydrogenating the resulting 7-octen-1-al and oxidizing the resulting n-octanal with oxygen.

Reductive amination of 7-octen-1-al (step ix)

Reductive amination of 7-octen-1-al with ammonia and hydrogen in the presence of a hydrogenation catalyst gives 7-octenamine. The catalyst may be any of those commonly used in hydrogenation reactions. More specifically, there may be mentioned, among others, Raney nickel, Raney cobalt, Raney copper and Raney iron; modified Raney nickel and modified Raney cobalt, modifiers being such metals as chromium, tungsten, molybdenum, rhenium, zirconium, manganese, titanium and iron; nickel-on-carrier, cobalt-on-carrier, copper-on-carrier and iron-on-carrier, carriers being diatomaceous earth, alumina, silica, acid clay, etc.; and partial modifications of the above carrier-supported catalysts, modifiers being such metals as manganese, cobalt, chromium and zirconium; as well as palladium-on-carbon, palladium-on-barium sulfate, palladium-on-barium carbonate, ruthenium-on-carbon, rhenium-on-carbon, copper chromite, molybdenum oxide and tungsten oxide. Especially preferred among them are nickel catalysts, palladium catalysts and copper chromite. With some hydrogenation catalysts, partial poisoning thereof with lead, lead compounds, sulfur or sulfur compounds, for instance, may result in inhibition of conversion of the starting aldehyde to the corresponding alcohol by hydrogenation, for instance. The hydrogenation catalyst is used in an amount of 0.001–1 gram atom, preferably 0.01–0.5 gram atom, as metal per mole of 7-octen-1-al. Liquid ammonia or ammonium hydroxide may be used as the ammonia source. Ammonia is preferably used in excess of 7-octen-1-al so as to prevent side reactions. Thus, ammonia is generally used in an amount of not less than 3 moles, preferably not less than 10 moles per mole of 7-octen-1-al. Although there is no critical upper limit to the amount of ammonia, it is generally used in an amount not exceeding 100 moles per mole of 7-octen-1-al for economic reasons. The hydrogen pressure is selected within the range of 1–300 kg/cm², preferably 5–200 kg/cm². The reaction temperature is selected within the range of from room temperature to 250° C., preferably 50°–200° C.

The reaction can be carried out either without any solvent or in the presence of a solvent inert to the reaction. Usable solvents include, among others, alcohols (e.g. methanol, ethanol, propanol, butanol), hydrocarbons (e.g. hexane, heptane, octane, benzene, toluene, xylene) and ethers (e.g. tetrahydrofuran, dioxane, diethyl ether). This reductive amination reaction may be carried out either in one step by reacting 7-octen-1-al with ammonia and hydrogen simultaneously or in two steps, namely by first reacting 7-octen-1-al with ammonia in the presence or absence of a condensing agent such as an ammonium ion-containing inorganic or organic ion exchanger and then hydrogenating the resulting imine. The two-step reaction has an advantage that an increased selectivity toward 7-octenamine can be obtained. In the reductive amination of 7-octen-1-al, it is desirable to stop the reaction when the consumption of hydrogen has reached the stoichiometric amount, whereby conversion of 7-octenamine to octylamine by hydrogenation can be prevented. When extremely high purity 7-octenamine is desired, it is preferable to suppress the conversion of 7-octen-1-al to 7-octenamine to a level not exceeding about 80%. Although the reaction can be carried out either batchwise or continuously, it is preferred from the industrial viewpoint to perform the reaction continuously using a known reactor such as a stirred tank reactor, a bubble tower reactor or a packed tower reactor. After the reaction, 7-octenamine can be recovered from the liquid reaction mixture by a conventional separation procedure.

7-Octenamine is a novel compound which has not been described in the literature. It is useful as an intermediate in synthesizing various useful materials such as ion exchange membranes, polymer modifiers, medicines, agricultural chemicals and dyes.

Having generally described this invention, a further understanding can be obtained by reference to certain specific examples which are provided herein for purpose of illustration only and are not intended to be limiting unless otherwise specified.

EXAMPLE 1

(Production of 7-octen-1-al)

A 50-ml four-necked flask equipped with distillation apparatus, dropping funnel, stirrer, thermometer and nitrogen gas inlet was charged with 0.2 g (1.0 weight percent based on the liquid reaction mixture) of a copper chromite catalyst "N203" ($CuO \cdot CuCr_2O_4$, 5% $MnO_2$; Nikki Chemical Co., Ltd.) and 20 g of 2,7-octadien-1-ol. The system was purged with nitrogen gas. The flask contents were then heated to and maintained at 180° C. While introducing nitrogen gas at the rate of 10 liters per hour, 20 g (0.159 mole) of 2,7-octadien-1-ol was added dropwise with stirring over 60 minutes. After completion of the dropping, stirring was continued under the same conditions for an additional 60 minutes. The distillate weighed 38 g. The 7-octen-1-al contained in the distillate amounted to 89 mole % based on the charged 2,7-octadien-1-ol. The distillate was fractionated under 500 mmHg to give 30.5 g of 7-octen-1-al as a fraction boiling at 159° C.–161° C. The structure of the 7-octen-1-al was confirmed by mass spectrographic analysis, infrared spectrographic analysis and NMR spectrographic analysis.

When the above procedure was repeated except that another copper chromite catalyst "T-531" (CuO.CuCr$_2$O$_4$; Nissan-Girdler Catalyst Co., Ltd.) was used, substantially the same results as above were obtained.

EXAMPLES 2-5 AND COMPARATIVE EXAMPLES 1-3

(Production of 7-octen-1-al)

The isomerization of 2,7-octadien-1-ol was carried out in the same manner as described in Example 1 except that the catalyst and the amount thereof as well as the atmosphere in the reaction system were varied. The results obtained are shown in Table 1, in which the percent isomerization to 7-octen-1-al means the ratio in mole percent of the 7-octen-1-al in the distillate to the charged 2,7-octadien-1-ol.

TABLE 1

| | Catalyst | | | % Isomerization to 7-octen-1-al |
|---|---|---|---|---|
| | Species | Amount[a] (wt %) | Atmosphere | |
| Example 2 | Copper chromite (G-22, 33% Cu, 27% Cr, 11% Ba; Nissan-Girdler Catalyst Co., Ltd.) | 1 | Nitrogen | 82 |
| Example 3 | Copper-chromium-zinc oxide (C—44; Catalysts & Chemicals Inc., Far East) | 1 | Nitrogen | 83 |
| Example 4 | Copper-zinc oxide (N211, CuO—ZnO; Nikki Chemical) | 1 | Nitrogen | 78 |
| Example 5 | Zinc chromite (C—72, ZnO.ZnCr$_2$O$_4$; Toyo Catalysts & Chemicals Inc., Far East) | 1 | Hydrogen | 76 |
| Comparative Example 1 | 3% Pd/C[b] (Nikki Chemical) | 0.5 | Hydrogen | 8 |
| Comparative Example 1 | 47% Ni/diatomaceous earth[c] (G-69RS; Nissan-Girdler) | 0.5 | Hydrogen | 7 |
| Comparative Example 3 | 3% Pd/C (Nikki Chemical) | 1 | Nitrogen | >1 |

Notes:
[a]Weight percent of catalyst metal based on the liquid reaction mixture.
[b]The catalyst contained 3 weight percent of metallic palladium supported on activated carbon.
[c]The catalyst contained 47 weight percent of metallic nickel supported on diatomaceous earth.

EXAMPLE 6

(Production of 7-octen-1-al)

A 100-ml three-necked flask equipped with stirrer, liquid and gas inlet and connected to distillation apparatus was charged with 30 ml of 2,7-octadien-1-ol (purity: not less than 99.9%) and 2.0 g of powdery copper chromite catalyst "N-203" (Nikki Chemical Co., Ltd.) and immersed in an oil bath maintained at 205° C. While passing nitrogen gas at the rate of 30 liters per hour with vigorous stirring, 2,7-octadien-1-ol was fed continuously at the rate of 170 ml/hr by means of a constant-rate feed pump. In this manner, the isomerization/distillation of 2,7-octadien-1-ol was conducted for 8 hours. The distillate amounted to about 170 ml per hour and accordingly the volume of the liquid flask contents was maintained at about 30 ml throughout the reaction period. After the reaction, the total distillate volume was 1,350 ml. Gas chromatographic analysis revealed that the distillate contained 16.9 mole percent of unreacted 2,7-octadien-1-ol, 2.7 mole percent of n-octanal, 8.9 mole percent of n-octanol and octen-1-ols, and 70.7 mole percent of 7-octen-1-al.

Purification of 1.0 kg of the distillate thus obtained in a glass distillation column with a theroretical plate number of 40 gave about 700 g of 7-octen-1-al (98% pure and containing about 2% of n-octanal) as a fraction boiling at 58° C./10 mmHg.

EXAMPLE 7

(Production of 7-octenoic acid)

(1) Production of 7-octen-1-al
The procedure of Example 6 was repeated.
(2) Production of 7-octenoic acid
A 100-ml four-necked flask equipped with thermometer, stirrer, reflux condenser, raw material inlet and oxygen gas inlet was charged with 30 ml of propionic acid and 32 mg (3.0 millimoles per liter of the liquid reaction mixture) of ferrous acetate, and the flask contents were warmed with stirring to complete dissolution. The microfeeder connected to the raw material inlet was charged with 50 ml of a 4 moles/liter solution of 7-octen-1-al in propionic acid preliminarily purged with nitrogen gas. When the temperature within the reactor reached 65° C., stirring of the contents was stirred at a rate of 800 rpm, and the propionic acid solution of 7-octen-1-al was fed continuously through the raw material inlet at a feed rate of 10 ml/hr for 3 hours while maintaining the temperature within the reactor at 65° C. and introducing oxygen gas at a flow rate of 10 liters per hour. After completion of the addition of 7-octen-1-al, stirring was continued at the same temperature for further 2 hours. Throughout the reaction period, the inside temperature was maintained at a constant level of 65° C. When the oxidation reaction was discontinued (5 hours from the start of the reaction), the conversion of 7-octen-1-al was 88% and the selectivity toward 7-octenoic acid (based on the converted 7-octen-1-al) was 85%. Gas chromatographic analysis of the reaction product indicated secondary formation of heptene, formic acid and so on, though in small amounts. Off-gas analysis at hourly intervals from the start of the reaction revealed that the carbon dioxide was formed in an amount of 3.5 mole % based on the converted 7-octen-1-al. The liquid reaction mixture obtained above was washed with 60 ml of 1N hydrochloric acid and distilled under reduced pressure to give 10 g of 7-octenoic acid as a fraction boiling at 98°-99° C./2 mmHg.

EXAMPLES 8–13

(Production of 7-octenoic acid)

Using 7-octen-1-al obtained in Example 7, step 1) together with different catalysts, solvents and oxygen-containing gases as given in Table 2 and varying catalyst amount, concentration of 7-octen-1-al in the feed solution, reaction temperature and reaction time as given in Table 2, the oxidation of 7-octen-1-al was performed in the same manner as described in Example 7, step 2). The results obtained are summarized in Table 2.

TABLE 2

| Example | Catalyst[1] (millimole(s)/l) | | Solvent | 7-OA[2] concn. (moles/l) | Oxygen containing gas (l/hr) | Reaction temperature (°C.) | Reaction time (hrs) | 7-OA conversion (%) | Selectivity toward 7-octenoic acid (%) |
|---|---|---|---|---|---|---|---|---|---|
| 8 | Fe(OAc)$_2$ | 3.0 | Butyric acid | 2.0 | Oxygen 10.0 | 65 | 5 | 85 | 84 |
| 9 | Cu(OAc)$_2$ | 2.0 | Propionic acid | 4.0 | Oxygen 10.0 | 65 | 5 | 88 | 83 |
| 10 | Ni(OAc)$_2$ | 1.0 | Acetic acid | 4.0 | Oxygen 10.0 | 50 | 4 | 92 | 81 |
| 11 | Mn(OAc)$_2$ | 0.5 | Propionic acid | 2.0 | Air 15.0 | 50 | 4 | 90 | 78 |
| 12 | Co(OAc)$_2$ | 0.5 | Capronic acid | 4.0 | Air 15.0 | 45 | 5 | 92 | 76 |
| 13 | Cu(OAc)$_2$ Mn(OAc)$_2$ | 1.0 1.0 | Valeric acid | 4.0 | Oxygen 10.0 | 50 | 5 | 95 | 80 |

Notes:
[1] Ac=acetyl group; catalyst concentration in millimoles per liter of the liquid reaction mixture.
[2] 7-OA=7-octen-1-al; concentration in moles per liter of the feedsolution in the same solvent as the reaction solvent.

EXAMPLE 14

(Production of 8-aminocaprylic acid)

(1) Production of 7-octen-1-al
The procedure of Example 6 was repeated.
(2) Production of 7-octenoic acid
The procedure of Example 7, step (2) was repeated.
(3) Production of 8-bromocaprylic acid
(i) A 1,000-ml three-necked flask equipped with hydrogen bromide inlet, thermometer and stirrer was charged with 100 g (0.7 mole) of 7-octenoic acid obtained in (2) above, 1 g of benzoyl peroxide and 600 ml of toluene. While maintaining the inside temperature at 5° C., hydrogen bromide was introduced with stirring at a rate of 20 liters per hour over 2 hours. The liquid reaction mixture was then washed with 100 ml of 0.1N aqueous sodium thiosulfate solution and 100 ml of water and then the toluene was distilled off. The residue was recrystallized from petroleum ether to give 143.6 g of 8-bromocaprylic acid (m.p. 35°–37° C.). The yield was thus 92% based on the charged 7-octenoic acid.

(ii) A 500-ml four-necked flask equipped with hydrogen bromide inlet, thermometer, 7-octenoic acid inlet and oxygen inlet was charged with 10 g of 7-octenoic acid and 50 ml of toluene. After passing air at 20° C. with stirring at a rate of 10 liters per hour for 30 minutes, hydrogen bromide and a solution of 90 g of 7-octenoic acid in 250 ml of toluene were continuously fed with stirring at the rates of 120 ml/hr and 9 l/hr, respectively. After 3 hours of reaction, the reaction mixture was treated in the same manner as described above under (3) (i) to give 139 g (89% yield) of 8-bromocaprylic acid.
(4) Production of 8-aminocaprylic acid
A 500-ml three-necked flask equipped with stirrer, thermometer and dropping funnel was charged with 400 ml of 25% aqueous ammonia, and the flask contents were maintained at 15° C. Thereto was added 50 g (0.22 mole) of molten 8-bromocaprylic acid over 30 minutes. After the addition, stirring was continued for further 10 hours. Thereafter, the ammonia was removed by warming the liquid reaction mixture. The mixture was then cooled and adjusted to pH 6.0 with 0.1N hydrochloric acid. The resulting crystalline precipitate was collected by filtration. The precipitate and the second crop obtained by concentration the mother liquor were combined and recrystallized from water to give 30 g of 8-aminocaprylic acid (m.p. 193°–195° C.). The yield was 86% based on the charged 8-bromocaprylic acid.

EXAMPLE 15

(Production of 8-cyanocaprylic acid)

(1) Production of 7-octen-1-al
The procedure of Example 6 was repeated.
(2) Production of 7-octenoic acid
The procedure of Example 7, step (2) was repeated.
(3) Production of 8-bromocaprylic acid
The procedure of Example 14, step (3) was repeated.
(4) Production of 8-cyanocaprylic acid
(i) A 500-ml three-necked flask equipped with thermometer and stirrer was charged with 100 g (0.45 mole) of 8-bromocaprylic acid, 0.5 g of 18-crown and 100 ml of water. Then, 23.8 g (0.224 mole) of sodium carbonate was added with stirring. After completion of the addition of sodium carbonate, B 44 g (0.68 mole) of potassium cyanide was added, and the reaction was allowed to proceed at 60° C. for 5 hours. Thereafter, the liquid reaction mixture was acidified by addition of concentrated hydrochloric acid and, following further addition of 50 g of ammonium sulfate, extracted with two 250-ml portions of ethyl ether. The ether layer was dried over anhydrous sodium sulfate and then the ether was distilled off. The residual liquid was distilled under reduced pressure to give 54.8 g (72% yield based on the charged 8-bromocaprylic acid) of 8-cyanocaprylic acid as a fraction boiling at 132°–136° C./0.8 mmHg.

(ii) The same reaction as described above under (3) (i) was carried out without adding 18-crown and there was obtained 47.9 g (63% yield based on the charged 8-bromocaprylic acid) of 8-cyanocaprylic acid.

EXAMPLE 16

(Production of 8-cyanocaprylic acid ester)

(1) Production of 7-octen-1-al
The procedure of Example 6 was repeated.
(2) Production of 7-octenoic acid
The procedure of Example 7, step (2) was repeated.
(3) Production of 8-bromocaprylic acid
The procedure of Example 14, step (3) was repeated.
(4) Production of ethyl 8-bromocaprylate
A 500-ml flask equipped with a liquid-liquid separating device for separation of water was charged with 100 g (0.45 mole) of 8-bromocaprylic acid, 100 ml of ethanol, 300 ml of benzene and 10 g of phosphoric acid, and the reaction was allowed to proceed under azeotropic removal of water for 6 hours. Thereafter, 200 ml of water and 200 ml of benzene were added to the liquid reaction mixture for extraction. The benzene layer was washed with two 100-ml portions of water and then dried over anhydrous sodium sulfate. After the benzene was distilled off, the residual liquid was distilled under reduced pressure to give 106 g (94% yield based on the charged 8-bromocaprylic acid) of ethyl 8-bromocaprylate as a fraction boiling at 124°–125° C./4 mmHg.

(5) Production of ethyl 8-cyanocaprylate (i) A 300-ml three-necked flask equipped with thermometer, stirrer and dropping funnel was charged with 100 ml of water, 78 g of sodium cyanide and 1.0 g of benzyltriethylammonium chloride, and the flask contents were maintained at 60° C. Thereto was added 100 g (0.4 mole) of ethyl 8-bromocaprylate dropwise with stirring over an hour. Thereafter, stirring was further continued for 3 hours. When the reaction mixture was cooled and allowed to stand, it separated into two layers. The upper layer was separated and washed twice with a small amount of water. Reduced pressure distillation gave 72 g (91% yield based on the charged ethyl 8-bromocaprylate) of ethyl 8-cyanocaprylate.

(ii) The same reaction apparatus as described above under (5) (i) was charged with 78 g of sodium cyanide, 200 ml of acetonitrile and 5 g of polyethylene glycol dimethyl ether (average molecular weight: 400), and the flask contents were maintained at 60° C. After addition of 100 g (0.4 mole) of ethyl 8-bromocaprylate over an hour with stirring, the reaction was continued for 3 hours. After the reaction, 400 ml of water and 400 ml of benzene were added for extraction of the reaction product with benzene. The benzene layer was washed with two 50-ml portions of water, and then the benzene was distilled off. The liquid residue was distilled under reduced pressure to give 71 g (90% yield based on the charged ethyl 8-bromocaprylate) of ethyl 8-cyanocaprylate as a fraction boiling at 127°–130° C./4 mmHg.

EXAMPLE 17

(Production of n-octanal)

(1) Production of 7-octen-1-al

The procedure of Example 6 was repeated.

(2) Production of n-octanal (i) A one-liter stainless steel autoclave equipped with magnetic stirrer, gas inlet and gas outlet was charged with 450 ml of ethyl alcohol, 150 ml (129.6 g) of the distillate from the above step and 6.6 g of a palladium-on-activated carbon catalyst "A" (5% palladium-on-carrier; Kawaken Fine Chemicals) and, while passing hydrogen gas at a flow rate of 20 liters per hour, the hydrogenation reaction was carried out with vigorous stirring at a temperature of 70° C. and a hydrogen pressure of 5 atmospheres for 2 hours. After removal of the catalyst by filtration, the liquid reaction mixture was analyzed by gas chromatography. No other peaks than those of n-octanal and n-octanol were detected at all. The n-octanal/n-octanol mole ratio was 74/26. After the ethyl alcohol was distilled off, the residue was fractionated by distillation under reduced pressure. There were obtained 94 g of n-octanal as a fraction boiling at 55° C./10 mmHg and 33 g of n-octanol as a fraction boiling at 87° C./10 mmHg. Apparently, no distillation residue was present.

(ii) The following run was carried out with another hydrogenation catalyst. A 100-ml three-necked flask equipped with a stirrer and a hydrogen gas inlet connected to a hydrogen gas reservoir equipped with a buret was charged with 20 ml (17.3 g) of the above distillate containing 7-octen-1-al, 20 ml of n-hexane and 0.5 g of a Raney nickel catalyst "NDT-65" (nickel content 45%; Kawaken Fine Chemicals), and the reaction was effected by stirring at room temperature and atmospheric pressure. With the progress of the reaction, hydrogen absorption began, and 3.85 liters of hydrogen was absorbed in 3.5 hours, when the reaction was stopped. The liquid reaction mixture was analyzed by gas chromatography. The n-octanal/n-octanol mole ratio was 69/31. No peaks for other products were detected.

EXAMPLE 18

(Production of caprylic acid)

(1) Production of 7-octen-1-al

The procedure of Example 6 was repeated.

(2) Production of n-octanal

The procedure of Example 17, step (2) was repeated.

(3) Production of caprylic acid

A 100-ml four-necked flask equipppped with thermometer, stirrer, reflux condenser, raw material inlet and oxygen inlet was charged with 30 ml of propionic acid and 32 mg (3.0 millimoles per liter of the liquid reaction mixture) of ferrous acetate, and the contents were warmed with stirring to completely dissolve the ferrous acetate. The microfeeder connected to the raw material inlet was charged with 50 ml of a 4 moles/l solution of n-octanal in propionic acid as preliminarily purged with nitrogen. While the reactor inside temperature was maintained at a constant level of 65° C., the oxidation reaction was carried out by continuously adding the solution of n-octanal in propionic acid via the raw material inlet at a feed rate of 10 ml/hr over 3 hours with stirring at 800 rpm while introducing oxygen gas at a flow rate of 10 liters per hour. After completion of the n-octanal addition, stirring was continued at the same temperature for an additional hour. The inside temperature was maintained at 65° C. throughout the reaction period. Gas chromatographic analysis revealed that the n-octanal conversion rates immediately after completion of the n-octanal addition (after 3 hours of reaction) and after completion of the oxidation reaction (after 4 hours of reaction) were 92% and 99%, respectively. The selectivity toward caprylic acid at the time of completion of the reaction was 95% (based on the converted n-octanal). Analysis of off-gas samples taken at hourly intervals from the start of the reaction revealed that the yield of carbon dioxide was 2.0 mole % (based on the converted n-octanal).

After the reaction, the liquid reaction mixture was washed with 60 ml of 1N hydrochloric acid and then with 120 ml of distilled water and subjected to fractional distillation under reduced pressure to give about 13 g of caprylic acid as a fraction boiling at 98°–100° C./2 mmHg.

EXAMPLES 19–25

(Production of caprylic acid)

n-Octanal was prepared by the procedure of Example 17 and oxidized in the same manner as described in Example 18, (3) except that the catalyst, amount thereof, solvent, concentration of n-octanal in the feed solution, oxygen-containing gas, reaction temperature and reaction time were as given in Table 3. The results obtained are shown collectively in Table 3.

TABLE 3

| Example | Catalyst[1] (millimole(s)/l) | | Solvent | n-OA concn.[2] (moles/l) | Oxygen containing gas (l/hr) | Reaction temperature (°C.) | Reaction time (hrs) | n-OA conversion[3] (%) | Caprylic acid selectivity (%) |
|---|---|---|---|---|---|---|---|---|---|
| 19 | Fe(OAc)$_2$ | 1.5 | Acetic acid | 4.0 | Oxygen 10 | 65 | 4 | 98 | 95 |
| 20 | Cu(OAc)$_2$ | 3.0 | Propionic acid | 4.0 | Oxygen 10 | 65 | 4 | 99 | 94 |
| 21 | Co(OAc)$_2$ | 1.0 | Butyric acid | 4.0 | Oxygen 10 | 50 | 3.5 | 99 | 92 |
| 22 | Mn(OAc)$_2$ | 1.0 | Valeric acid | 2.0 | Air 15 | 50 | 4 | 99 | 89 |
| 23 | Fe(OAc)$_2$ | 3.0 | Caprylic acid | 4.0 | Oxygen 10 | 65 | 4 | 98 | 94 |
| 24 | Mn(OAc)$_2$ Cu(OAc)$_2$ | 1.0 1.0 | Propionic acid | 4.0 | Oxygen 10 | 50 | 4 | 99 | 90 |
| 25 | Ni(OAc)$_2$ | 1.0 | Propionic acid | 2.0 | Oxygen 10 | 50 | 4 | 99 | 90 |

Notes:
[1] Ac=acetyl; catalyst concentration in millimole(s) per liter of the liquid reaction mixture.
[2] n-OA=n-octanal; concentration in moles per liter of the feed solution. The solvent was the same as the reaction solvent.
[3] Percent conversion at the time when the reaction was stopped.

EXAMPLE 26

(Production of 7-octenamine)

(1) Production of 7-octen-1-al
The procedure of Example 6 was repeated.

(2) Production of 7-octenamine (i) A one-liter autoclave with a magnetic stirrer was charged with 5 g of a copper chromite catalyst "N203" (CuO-Cr$_2$O$_3$, 5% MnO$_2$; Nikki Chemical), 40 g of 7-octen-1-al, 150 g of ethanol and 150 g of ammonia. Then, hydrogen was introduced to a pressure of 80 kg/cm$^2$. The autoclave was heated to 150° C. over an hour and thereafter the reaction was continued at 150° C. for further 2 hours. After the reaction, the autoclave was cooled, the unreacted hydrogen and ammonia were released, and the contents were taken out. The catalyst was filtered off, the solvent was distilled off, and the residual liquid was distilled under reduced pressure using a reduced pressure distillation apparatus equipped with a fractionation column. There was obtained 28 g of the product as a fraction boiling at 79°–81° C./20 mmHg. Gas chromatographic analysis of this fraction showed that it had a purity of 98% and contained 2% of octylamine. The fraction was then subjected to mass, infrared and NMR spectrographic analysis, whereby the product was identified as 7-octenamine. The infrared and NMR spectral data are as follows:

Infrared spectrum (neat):
  $V_{NH_2}$; 3350 cm$^{-1}$, 1570 cm$^{-1}$
  $V_{CH=CH_2}$; 1640 cm$^{-1}$, 990 cm$^{-1}$, 905 cm$^{-1}$
NMR spectrum (CDCl$_3$)   δ (ppm)

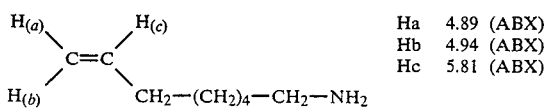

| | |
|---|---|
| Ha | 4.89 (ABX) |
| Hb | 4.94 (ABX) |
| Hc | 5.81 (ABX) |
| Hd | 2.00 (Triplet with fine line structure overlapping) |
| He | 1.45 (Singlet with fine line structure) |
| Hf | 2.62 (Triplet with fine line structure overlapping) |
| Hg | 1.51 (Medium broad singlet) |

$J_{Ha}$—Hc = 10.5 Hz
$J_{Hb}$—Hc = 17.2 Hz
$J_{Hc}$—Hd = 6.8 Hz
$J_{Ha}$—Hb = 1.5 Hz
$J_{Hd}$—He = 6.8 Hz (ii) A 100 ml autoclave with a magnetic stirrer was charged with 0.5 g of a Raney nickel catalyst (nickel content 53 weight %), 4 g of 7-octen-1-al, 20 g of ethanol, 4 g of water and 12 g of ammonia. Hydrogen was introduced into the autoclave at room temperature to 30 atmospheres. While maintaining the inside temperature at 35° C., the reaction was carried out with stirring. Approximately the theoretical amount of hydrogen was absorbed in 7 hours, when the reaction was stopped. The unreacted hydrogen and ammonia were released, and the liquid reaction mixture was analyzed by gas chromatography. It was revealed that the yield of 7-octenamine was 3.0 g (76% based on the charged 7-octen-1-al). As a byproduct, 0.4 g of the condensation product (Schiff base) of 7-octenamine with 7-octen-1-al was found and, when treated with diluted hydrochloric acid, yielded 7-octenamine hydrochloride and 7-octen-1-al; the 7-octen-1-al forming the organic layer was separated and the aqueous layer was made basic with sodium hydroxide to give 0.2 g of 7-octenamine.

(iii) The same reaction apparatus as described above under (ii) was charged with 1 g of Lindler catalyst, 4 g of 7-octen-1-al, 10 g of tetrahydrofuran and 20 g of ammonia. Hydrogen was introduced into the autoclave to 50 atmospheres. The reaction was then carried out with stirring at 80° C. (inside temperature) for 4 hours. After the reaction, the unreacted hydrogen and ammonia were released. Gas chromatographic analysis of the liquid reaction mixture indicated that B 7-octenamine was formed in an amount of 2.9 g (71% yield based on the charged 7-octen-1-al).

EXAMPLE 27

(Production of 7-octen-1-ol)

(1) Production of 7-octen-1-al

The procedure of Example 6 was repeated.

(2) Production of 7-octen-1-ol (i) A 100-ml autoclave with a magnetic stirrer was charged 0.25 g of a copper chromite catalyst "N203" (Nikki Chemical), 30 g of ethanol and 5 g of 7-octen-1-al. Hydrogen was introduced into the autoclave to 35 atmospheres, and the inside temperature was raised to 110° C. with stirring over 30 minutes and maintained at that temperature for 2 hours. Then, the autoclave was cooled, the hydrogen was released, and the contents were taken out. Gas chromatographic analysis of the liquid reaction mixture showed that the conversion of 7-octen-1-al was 73% and the selectivity toward 7-octen-1-ol was 99% based on the converted 7-octen-1-al.

(ii) The above procedure (i) was repeated except that 0.25 g of a zinc chromite catalyst "C-72" (Toyo Catalysts & Chemicals) was used in place of the copper chromite catalyst. The conversion of 7-octen-1-al was 67% and the selectivity toward 7-octen-1-ol was 100% based on the converted 7-octen-1-al.

COMPARATIVE EXAMPLE 4

The hydrogenation of 7-octen-1-al was carried out under the same conditions as described under (2) (i) in Example 27 except that the reaction temperature was 180° C. No formation of 7-octen-1-ol was observed but n-octanol was formed in 92% yield.

COMPARATIVE EXAMPLE 5

The hydrogenation of 7-octen-1-al was carried out under the same conditions as described under (2) (i) in Example 27 except that 0.5 g of Raney nickel (Ni content 53%) was used in place of the copper chromite catalyst. No formation of 7-octen-1-ol was observed but n-octanol was formed in 99% yield.

What is claimed is:

1. A process for producing 7-octen-1-al which comprises isomerizing 2,7-octadiene-1-ol in the presence of a catalyst comprising oxides of at least two metals selected from the group consisting of copper, chromium and zinc at a reaction temperature of 100°–250° C.

2. A process according to claim 1, wherein the catalyst is copper chromite, copper-zinc oxide, zinc chromite or copper-chromium-zinc oxide.

3. A process for producing n-octanal which comprises the steps of:
   isomerizing 2,7-octadiene-1-ol in the presence of a catalyst comprising oxides of at least two metals selected from the group consisting of copper, chromium and zinc at a reaction temperature of 100°–250° C., and
   hydrogenating the resulting 7-octen-1-al in the presence of hydrogen and a hydrogenation catalyst for carbon-to-carbon double bond hydrogenation.

4. A process for producing 7-octen-1-ol which comprises the steps of:
   isomerizing 2,7-octadien-1-ol in the presence of a catalyst comprising oxides of at least two metals selected from the group consisting of copper, chromium and zinc at a reaction temperature of 100°–250° C., and
   hydrogenating the resulting 7-octen-1-al at a temperature of 70°–150° C. in the presence of hydrogen and a chromium oxide catalyst.

* * * * *

UNITED STATES PATENT AND TRADEMARK OFFICE
CERTIFICATE OF CORRECTION

PATENT NO. : 4,510,331

DATED : April 9, 1985

INVENTOR(S) : Noriaki Yoshimura et al

It is certified that error appears in the above-identified patent and that said Letters Patent is hereby corrected as shown below:

On page 1, after Field [22], insert a new Field:

--[30]  Foreign Application Priority Data

| | | | | |
|---|---|---|---|---|
| Jul. | 2, 1981 | [JP] | Japan | 104199/1981 |
| Dec. | 17, 1981 | [JP] | Japan | 204997/1981 |
| Dec. | 28, 1981 | [JP] | Japan | 212566/1981 |
| Jan. | 11, 1982 | [JP] | Japan | 2962/1982 |
| Mar. | 17, 1982 | [JP] | Japan | 43622/1982 |
| Apr. | 2, 1982 | [JP] | Japan | 55882/1982 |
| Apr. | 2, 1982 | [JP] | Japan | 55883/1982--; |

At column 2, line 28, change "Reduction amination" to --Reductive amination--;

At column 2, line 31, change "n-Otanal" to --n-Octanal--;

At column 4, line 14, change "selectively" to --selectivity--;

At column 4, line 41, delete "the";

At column 10, line 23, change "7-borabicyclononane" to --9-borabicyclononane--.

At column 13, line 36, TABLE 1, change ">1" to --<1--.

UNITED STATES PATENT AND TRADEMARK OFFICE
CERTIFICATE OF CORRECTION

PATENT NO. : 4,510,331
DATED : April 9, 1985
INVENTOR(S) : Noriaki Yoshimura et al It is certified that error appears in the above-identified patent and that said Letters Patent is hereby corrected as shown below:

At column 16, line 40, delete "B"; and

At column 20, line 41, delete "B".

Signed and Sealed this

Eighteenth Day of February 1986

[SEAL]

Attest:

Attesting Officer

DONALD J. QUIGG

Commissioner of Patents and Trademarks